(12) United States Patent
Mougin et al.

(10) Patent No.: US 7,862,805 B2
(45) Date of Patent: Jan. 4, 2011

(54) COSMETIC COMPOSITION FORMING AFTER APPLICATION A SUPRAMOLECULAR POLYMER

(75) Inventors: Nathalie Mougin, Paris (FR); Aude Livoreil, Paris (FR); Jean Mondet, Aulnay Sous Bois (FR)

(73) Assignee: L'Oreal, Paris (FR)

( * ) Notice: Subject to any disclaimer, the term of this patent is extended or adjusted under 35 U.S.C. 154(b) by 1408 days.

(21) Appl. No.: 10/479,716

(22) PCT Filed: Jun. 7, 2002

(86) PCT No.: PCT/FR02/01966

§ 371 (c)(1),
(2), (4) Date: Dec. 5, 2003

(87) PCT Pub. No.: WO02/098377

PCT Pub. Date: Dec. 12, 2002

(65) Prior Publication Data

US 2004/0161394 A1    Aug. 19, 2004

(30) Foreign Application Priority Data

Jun. 7, 2001 (FR) .................................. 01 07476

(51) Int. Cl.
*A61Q 1/04* (2006.01)
*A61Q 1/06* (2006.01)
*A61Q 1/08* (2006.01)
*A61Q 1/10* (2006.01)
*A61Q 1/12* (2006.01)
*A61Q 1/14* (2006.01)
*A61Q 5/02* (2006.01)
*A61Q 5/06* (2006.01)
*A61Q 5/10* (2006.01)

(52) U.S. Cl. .............................. 424/64; 424/63; 424/69; 424/70.1; 424/70.6; 424/70.7; 424/70.11; 424/70.12; 424/70.16; 424/401

(58) Field of Classification Search ....................... None
See application file for complete search history.

(56) References Cited

U.S. PATENT DOCUMENTS

| 3,784,488 | A | 1/1974 | Steinhauer et al. |
| 5,919,441 | A | 7/1999 | Mendolia et al. |
| 5,958,390 | A | 9/1999 | Sanner et al. |
| 5,998,570 | A | 12/1999 | Pavlin et al. |
| 6,051,216 | A | 4/2000 | Barr et al. |
| 6,399,048 | B1 | 6/2002 | Allard et al. |
| 6,432,423 | B1 | 8/2002 | Maignan et al. |
| 6,436,412 | B1 | 8/2002 | Quinn |
| 6,534,072 | B2 | 3/2003 | Mondet et al. |

FOREIGN PATENT DOCUMENTS

| DE | 15 95 016 | 3/1970 |
| EP | 0 868 906 | 10/1998 |
| EP | 1 155 687 | 11/2001 |
| FR | 2 034 760 | 12/1970 |
| FR | 2 765 480 | 1/1999 |
| FR | 2 772 771 | 6/1999 |
| WO | 98 14504 | 4/1998 |
| WO | 01 11956 | 2/2001 |
| WO | 03/032929 | 4/2003 |
| WO | 2004/016598 | 2/2004 |

*Primary Examiner*—Jyothsna A Venkat
(74) *Attorney, Agent, or Firm*—Oblon, Spivak, McClelland, Maier & Neustadt, L.L.P.

(57) ABSTRACT

The present invention relates to a care, and/or treatment, and/or make-up cosmetic composition for keratin materials, comprising, in a physiologically acceptable medium, an efficient amount of at least one linear, branched or cyclic polymer, or dendrimer, comprising:

a -POL- polymeric backbone comprising at least two repeating patterns, and at least two binding groups (A), attached on the polymeric backbone and adapted to create H links with one ore more partner binding groups, of an identical or different chemical nature, each coupling of two binding groups involving at least three H links.

13 Claims, No Drawings

COSMETIC COMPOSITION FORMING AFTER APPLICATION A SUPRAMOLECULAR POLYMER

The present invention generally relates to a care and/or treatment and/or make up cosmetic composition for keratin materials, having an increased persistence of at least one cosmetic and/or care effect provided after application by the composition, a good adhesion after application on keratin materials, and allowing for a quick, complete and selective make-up removal.

In particular, such a composition may be film-forming, and may lead after application to a film formation with the composition during drying.

In fact, in cosmetics, it is desirable to obtain a deposit on hair, skin, eye-lashes and nails, said deposit being often film-forming and providing:
- either hairstyle shaping (hair);
- or colour (hair, make-up);
- or gloss or gloss and colour (lipsticks, mascaras, eyeliners and nail varnish);
- or colour and a mat aspect (foundation cream), the loss of the mat aspect being most often due to the evolution of the colour provided under the effect of sebum and/or sweat secretion, making the skin shine;
- or care, if the deposit contains a care active ingredient, for example moisturizing, deodorant, sunscreen agents, etc.

Consequently, for some persistence of the effect being offered (colour, gloss, mat aspect, care) a large remanence of the cosmetic deposit is desired which should more particularly:
- be resistant to mechanical attacks such as frictions, transfers through contact with another object;
- be resistant to water, sweat, tears, rain; and
- be resistant to sebum and oils.

This is particularly true in make-up field for:
- lipsticks when an extended retention of the colour and gloss and the non transfer of the colour are looked for;
- foundation creams, eye-lid make-ups and powders where a retention of the colour provided is also looked for, keeping as long as possible the mat aspect of the initial shade despite sebum and sweat secretion as well as the non transfer.

In particular, in the case of make-up compositions, it would be highly desirable to have available coloured compositions having an increased consistency of the colour, i.e. where the colour is not degraded or made dull through mechanical attacks, water, sweat, tears, rain, sebum and oils, while keeping their other properties such as colour retention, gloss, mat aspect and care.

Moreover, it would be extremely desirable that such compositions, having an increased persistence for the effects being provided (especially colour, gloss, mat aspect, care), enhance the adhesion on keratin materials while making make-up removal easier.

The man of the art knows the use of conventional film-forming compounds, such as waxes, covalent link polymers and block polymers for the persistence of the cosmetic and/or care effect.

Thus, Patent EP-0 206 671 discloses a cosmetic composition comprising a copolymer of a fluoroalkyl(meth)acrylate and a linear alkyl(meth)acrylate and a volatile oil. The copolymer imparts to the cosmetic composition, when applied to the skin, an excellent water and oil resistance, allows for the composition to be homogeneously spread and leads to a film with a satisfactory adhesion and a high friction resistance. Additionally, the copolymers may be formulated as solid products, such as sticks or oily pencils having an extremely pleasant touch and the film-forming property of the copolymers and the retention effect for the make-up condition of the resulting film are both satisfactory.

European Patent Application EP-0 815 836 discloses a cosmetic composition comprising a fluoroalkyl(meth)acrylate copolymer and a solid oily substance which, after application, shows an excellent gloss and keeps a good gloss and colour over an extended time period. Such a composition may be used as a lipstick or mascara.

U.S. Pat. No. 5,948,393 discloses a water-in-oil make-up cosmetic composition comprising a colouring material in an internal phase and a fat soluble resin in an external phase. The fat soluble resin could be a fluororesin, a silicone resin, an aromatic hydrocarbon resin, a terpene resin, polybutene, polyisoprene, an alkyd resin and a polyvinylpyrrolidone modified polymer. The resulting make-up composition has a higher water, sweat, sebum and oil resistance.

U.S. Pat. No. 5,945,108 discloses a cosmetic composition, particularly a make-up cosmetic composition, containing a water and oil repellent powder obtained through treating the powder surface with a homopolymer or a copolymer comprising repeating (meth)acrylate patterns containing a polyfluoroalkyl group. The (meth)acrylic copolymers in the document may comprise the following monomer combinations:
- (meth)acrylates containing polyfluoroalkyl and alkyl (meth)acrylate groups;
- (meth)acrylates containing polyfluoroalkyl and silicone macromonomer groups; and
- (meth)acrylates containing polyfluoroalkyl, alkyl(meth)acrylate and silicone macromonomer groups.

The cosmetic compositions prepared through formulating such powders have higher water and oil repellent and comfort properties and prevent make-up degradations.

However, there is still a need for cosmetic compositions leading, after application on keratin materials, to deposits allowing for reconciling the cosmetic and/or care effect persistence, a good adhesion of the composition on keratin materials and a quick and complete make-up removal.

However, the Applicant has surprisingly found that a cosmetic composition comprising a polymer having a polymeric backbone comprising at least two repeating patterns and at least two binding groups attached onto the polymeric backbone, each binding group being adapted to interact with each partner binding group through the formation of at least 3H links, has an effect of increasing the persistence of at least one cosmetic and/or care effect provided after application on keratin materials by the composition.

It is meant under binding group, as defined in the present invention, any functional group comprising H link donor or acceptor groups, also called patterns.

It is meant under partner binding group, as defined in the present invention, any binding group of a polymer according to the invention adapted to create H links with one or more binding groups of another polymer according to the invention. The binding groups may have an identical or a different chemical nature. If they are identical, they can then create H links between each other. If they are different, they are selected so as to be complementary with respect to the H interactions.

The Applicant has also discovered that such a composition enhances the adhesion on keratin materials. In fact, keratin comprises groups adapted to create hydrogen interactions. Consequently, using in a cosmetic composition polymers comprising groups able each to create strong and multiples hydrogen interactions strongly enhances the adhesion of the composition on keratin.

Additionally, the Applicant has also discovered that using a selective make-up adapted to enter the deposit and break selectively the created interactions allows for a quick, complete and selective make-up removal.

Finally, the Applicant has discovered that using such polymers in a cosmetic composition leads, after application of such a composition on keratin materials, to the formation of a supramolecular polymer.

It is meant under supramolecular polymer, as defined in the present invention, a polymeric chain or network resulting from the assembly of a polymer according to the invention with at least another polymer according to the invention, each assembly comprising at least one pair of coupled binding groups.

It is meant under pair of coupled binding groups, as defined in the present invention, two binding groups belonging each to a polymer according to the invention linked together via at least three H links.

When the polymer is formulated in the presence of volatile solvents, it is possible to obtain a film formation with the composition during drying, when the polymer structure makes it possible.

It is meant under film formation, as defined in the present invention, the formation of physically cross-linked networks as films and having mechanical properties similar to those of high molecular weight polymers or chemically cross-linked networks. The physical cross-linking will provide the retention and persistence of the cosmetic and/or care effect in the same way as the chemical cross-linking, while allowing for reversibility, i.e. a possibility to totally remove the deposit via a specific make-up remover, which the chemical cross-linking does not allow.

It is known to the man of the art to use, in compositions comprising a liquid fatty phase, polymers comprising groups adapted to create hydrogen links, in order to structure the fatty phase.

Thus, U.S. Pat. No. 5,919,441, U.S. Pat. No. 5,981,680 and U.S. Pat. No. 6,051,216 as well as the International Patent Application WO 99/06473 disclose a composition comprising a silicone oil gelled by a polyorganosiloxane comprising groups adapted to give H interactions, including ester, amide, urethane, urea, thiourea groups and the combinations thereof. However, such H interaction group carrying polyorganosiloxanes are only used for gelling of the silicon oil based medium.

Similarly, U.S. Pat. No. 5,998,570 and the International Patent Application WO 00/40216, disclose polymers comprising groups adapted to create hydrogen links. Each of such groups is however only adapted to create one or two H links. Such polymers are used for gelling of the hydrocarbon oils.

None of those documents relates to a cosmetic composition comprising a polymer carrying at least two binding groups adapted to implement each at least three H interactions. Moreover, there is no mention in such documents as to the properties provided after application of the composition, such as an increased persistence of at least one cosmetic and/or care effect, a good adhesion of the composition on keratin materials and a possibility to reach a quick, complete and selective make-up removal.

Further, the International Patent Application WO-98/14504 discloses polymers comprising at least two groups adapted to create each four H interactions, reversible with the temperature. Such polymers are primarily used for their easier heat implementation, especially at a temperature where the molecules individually behave towards each other, without being involved in links. There is no mention about a cosmetic use of such polymers and the specific problems thereof.

An object of the invention is therefore to provide a care and/or treatment and/or make-up cosmetic composition for keratin materials allowing for overcoming those disadvantages.

More precisely, the object of the invention is to provide a care and/or treatment and/or make-up cosmetic composition for keratin materials comprising, in a physiologically acceptable medium, an efficient amount of at least one linear, branched, or cyclic polymer, or dendrimer, comprising:
 a polymeric backbone -POL- comprising at least two repeating patterns, and
 at least two binding groups (A) attached onto the polymeric backbone and adapted to create H links with one or more partner binding groups, of an identical or different chemical nature, each coupling of two binding groups involving at least three H links.

It is meant under polymeric backbone, as defined in the present invention, a polymer comprising at least two covalent repeating patterns.

Both binding groups (A) may be located sidewise in the polymeric chain or at the ends of the polymeric chain.

The binding groups (A) comprise H link donor and/or acceptor groups, also called patterns, and selected amongst the following chemical functions:

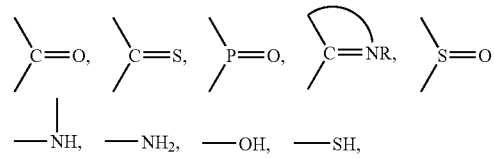

wherein R represents:
 a hydrogen atom, or
 an aryl group, or
 an aralkyl group, i.e. an aryl group substituted by a saturated, linear or branched hydrocarbon chain, comprising from 1 to 40 carbon atoms, or
 a saturated, linear, branched or cyclic hydrocarbon chain, comprising from 1 to 4 carbon atoms, and/or optionally comprising one or more heteroatoms selected amongst O, S and N, and/or optionally substituted by one or more fluorine atoms and/or hydroxy moieties.

Preferably, the patterns are selected amongst adenine, guanine, cytidine, thymine, pterine, ureidopyrimidone, melamine, cyanuric acid, maleimide, phthalhydrazine, isoguanine, glycoluril, uracil, acylaminopyridine, acylaminotriazine, pyridine/phenol, urazole, glutarimide, urazoylbenzoic acid groups.

Advantageously, such polymers have a polymeric backbone with a polymerisation degree ranging from 2 to 10000, and preferably from 10 to 5000.

Structure of the Polymer According to the Invention

The polymers according to the invention will be represented by:

A-POL-A wherein:
 A means a binding group
 POL means the polymeric backbone.

The polymers according to the invention may have various structures.

Generally speaking, they may be:

linear or branched and functionalised only at the ends:

linear or branched and comprising at least two groups within the chain:

or

(here one group at one end)

linear and comprising the A groups in side branches:

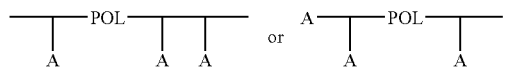

hyperbranched or dendrimeric with the A groups at the ends:

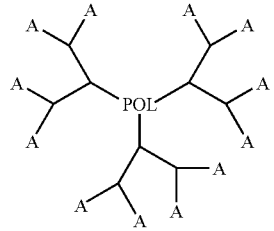

or star-shaped:

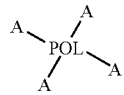

The preferred structures of the polymers according to the invention are:

1. Linear and α, ω Functional Polymers:

(only two groups)

Using such polymers in a cosmetic composition leads after application of the composition onto keratin materials to the formation of a supramolecular polymer as a long polymeric chain (with a high molecular weight). The polymers according to the invention are added end to end through coupling each of their binding groups with a chemically identical or self-complementary binding group (A), of another polymer:

2. Tri- or Multifunctional Polymers:

trifunctional: multifunctional with side A groups

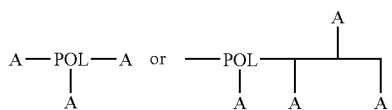

The tri- or multifunctional polymers, used alone or as a blend with difunctional polymers, can lead, after application of the composition onto keratin materials, to the formation of a supramolecular polymer comprising a physically cross-linked network, under a film aspect, and having a very good mechanical and solvent resistance. Such films may be selectively removed (make-up removal) by a solvent containing a H interaction breaker and adapted to penetrate into the deposit. The thus formed networks may be schematically represented as follows:

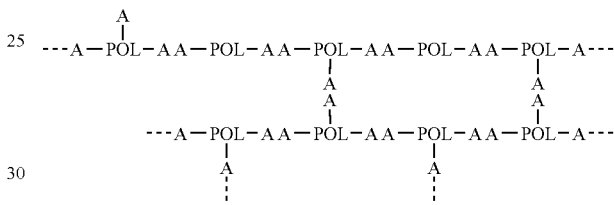

3. Star-Shaped, Hyperbranched or Branched Polymers (Particular Case of the Multifunctional Ones)

When used in a mixture with difunctional polymers, such polymers may lead, after application of the composition onto keratin materials, to the formation of a supramolecular polymer comprising a physically cross-linked network, identical to the networks obtained from tri- or multifunctional polymers, but with a better cross-linking probability, allowing for a lower polymer amount to be used for an identical cross-linking efficiency. The thus formed networks may be schematically represented as follows:

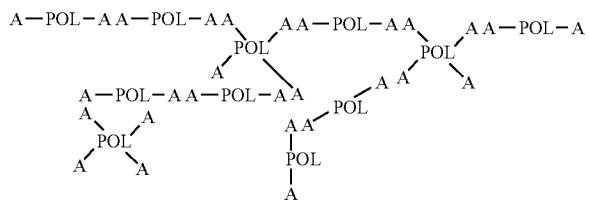

4. Polymer Blends with Identical Binding Groups (A) but with Their Polymeric Backbones Being of a Different Chemical Nature Using, in a cosmetic composition, polymer blends with identical or complementary A binding groups but with their polymeric backbones being of a different chemical nature may lead, after application of the composition onto keratin materials, to the formation of copolymer type assemblies, but with physical links between the patterns instead of covalent links.

Thus, one would obtain, after the deposit of a composition comprising two α,ω bifunctional polymers (respectively with -POL$_1$- and -POL$_2$- polymeric structure) a supramolecular polymer represented by:

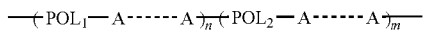

The polymer chainings in the supramolecular polymer are random in the present case and are equivalent to statistical assemblies.

It is however possible to obtain supramolecular polymers equivalent to alternate, blocked, multiblocked or grafted polymers, in the same way as in covalent polycondensation.

According to the invention, the supramolecular polymers are preferably statistical and obtained through a combination of -POL$_1$- and -POL$_2$- polymeric backbones such as:
- -POL1- is hydrophobic, and -POL$_2$- is hydrophilic, so as to set the hydrophilic/hydrophobic balance of the deposit, its water, sweat, sebum, oil resistance, etc.;
- the mixture of A-POL$_1$-A and A-POL$_2$-A polymers is initially soluble or adapted to be carried in predetermined solvents; and
- the final deposit has predetermined mechanical properties, for example, through combination of a hard -POL$_1$- polymeric backbone with a soft -POL$_2$- polymeric backbone.

A Binding Groups

The binding groups (A) necessarily comprise one or more functions selected amongst:

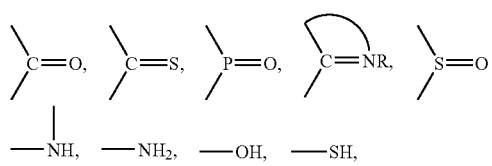

wherein R represents:
- a hydrogen atom, or
- an aryl group, or
- an aralkyl group, i.e. an aryl group substituted by a saturated hydrocarbon chain, linear or branched, comprising from 1 to 40 carbon atoms; or
- a saturated, linear, branched or cyclic hydrocarbon chain, comprising from 1 to 40 carbon atoms, and/or optionally comprising one or more heteroatoms selected amongst O, S and N, and/or optionally substituted by one or more fluorine atoms and/or hydroxy moieties.

Preferably, the A binding groups comprise 5, 6 atom rings (unsaturated aromatic or heterocyclic rings), quite often consisting in C and N atoms and with conjugated double links so as to stabilize and control the H interactions.

The self-complementary binding groups (A) are selected amongst the adenine, guanine, cytidine, thymine, pterine, ureidopyrimidone, melamine, cyanuric acid, maleimide, phthalhydrazine, isoguanine, glycoluril, uracil, acylaminopyridine, acylaminotriazine, pyridine/phenol, urazole, glutarimide, urazoyl benzoic acid groups.

Each partner group (A$_1$) should be adapted to create H links with one or more partner groups, whether identical (A$_1$) or different (A$_2$), so that each coupling of two partner groups will occur through formation of at least three H links, preferably four H links.

a) Example of Identical Groups (A$_1$) Adapted to Create Between Each Other at Least Three H Links: the Ureidopyrimidone Groups

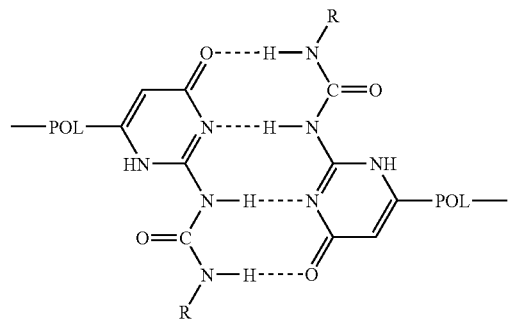

wherein R represents H or a C$_1$-C$_{40}$ linear or branched alkyl group adapted to contain one or more atoms such as O, S, N, P, F, Si, able to contain conjugated or non conjugated unsaturations, or R represents either a C$_4$-C$_8$ cycloalkyl group, or an aryl group, or a C$_1$-C$_{40}$ alkoxy group or an arylkoxy group, or an alkyl ester group.

Such groups interact with each other creating therebetween four H links.

b) Example of Groups (A$_1$) et (A$_2$) of a Different Chemical Nature, but Complementary with Respect to the Creation of at Least Three H Links: A$_1$=melamine and A$_2$=cyanuric acid

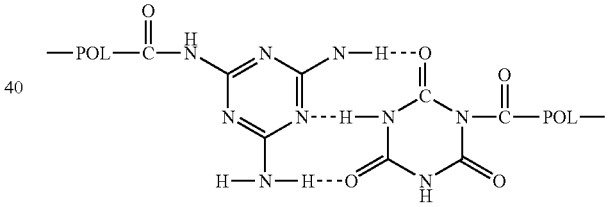

A$_1$ = mélanine    A$_2$ = acide cyanurique

Amongst or in addition to the mentioned binding groups (A), the following binding groups are preferred:

1. Bis(acylamino)pyridine of the Following Structure (I):

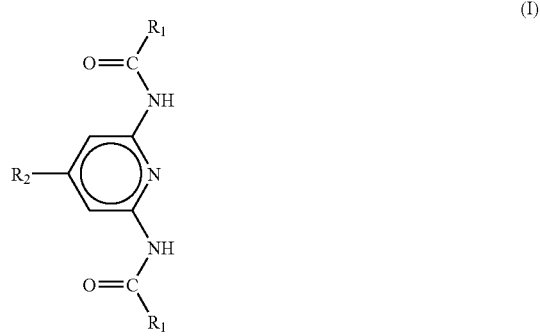

wherein:

$R_1$ and $R_2$ means H or a $C_1$-$C_{40}$ linear or branched alkyl adapted to contain one or more atoms such as O, S, N, P, Si, able to contain conjugated or non conjugated unsaturations, or $R_1$ and $R_2$ represent a $C_4$-$C_8$ cycloalkyl group or a $C_1$-$C_{40}$ aryl or alkoxy group, or an aryloxy group, or an alkyl ester group;

the attachment of the -POL- polymeric bakbone may occur in $R_1$ or $R_2$,

Such a binding group (A) may interact with itself, giving then four H interactions, but it often interacts with a complementary group and then give three H links.

Complementary Groups of the bis(acylamino)pyridine Group uracil having the structure (II):

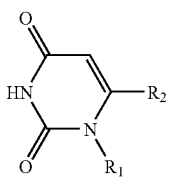

(II)

wherein:

$R_1$ and $R_2$ have the same meaning as previously defined, the -POL- polymeric backbone is attached in $R_1$ or $R_2$.

succinimide having the structure (III):

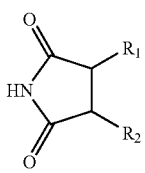

(III)

wherein:

$R_1$ and $R_2$ have the same meaning as previously defined, the -POL- polymeric backbone is attached in $R_1$ or $R_2$.

thymine (either substituted or not) having the structure (IV):

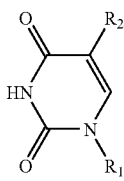

(IV)

wherein:

$R_1$ and $R_2$ have the same meaning as previously defined, the -POL- polymeric backbone is attached in $R_1$ or $R_2$.

glutarimide having the structure (V):

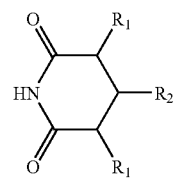

(V)

wherein:

$R_1$ and $R_2$ have the same meaning as previously defined, the -POL- polymeric backbone is attached in $R_1$ or $R_2$.

Cyanuric acid having the structure (VI):

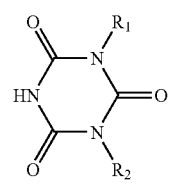

(VI)

wherein:

$R_1$ and $R_2$ have the same meaning as previously defined, the -POL- polymeric backbone is attached in $R_1$ or $R_2$.

2. Ureidopyrimidone Having the Structure (VII):

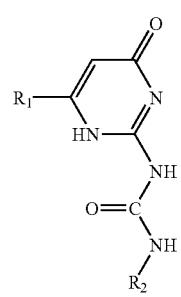

(VII)

wherein:

$R_1$ and $R_2$ have the same meaning as previously defined, the -POL- polymeric backbone is attached in $R_1$ or $R_2$.

Such binding groups interact with themselves creating therebetween four H links.

3. 2,4-diamino-s-triazine bis acyl Having the Structure (VIII):

(VIII)

wherein:

R₁ and R₂ have the same meaning as previously defined, the -POL- polymeric backbone is attached in R₁ or R₂.

Such binding groups interact with themselves creating therebetween four H links.

4. Ureidotriazine Having the Structure (IX):

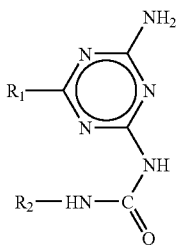

(IX)

wherein:

R₁ and R₂ have the same meaning as previously defined, the -POL- polymeric backbone is attached in R₁ or R₂.

Such binding groups interact with themselves creating therebetween four H links.

5. Phthalhydrazine Having the Structure (X):

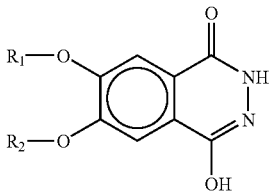

(X)

wherein:

R₁ and R₂ have the same meaning as previously defined, the -POL- polymeric backbone is attached in R₁ or R₂.

Such binding groups interact with themselves creating therebetween four H links.

6. Urazoylbenzoic acid Having the Structure (XI):

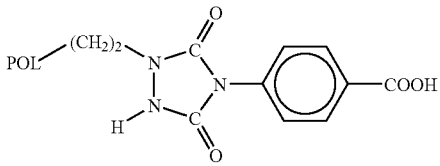

(XI)

wherein:

R₁ and R₂ have the same meaning as previously defined, the -POL- polymeric backbone is attached in R₁ or R₂.

Such binding groups interact with themselves creating therebetween four H links.

7. 2,4-diamino-s-triazine Having the Structure (XII):

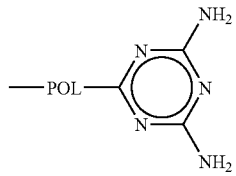

(XII)

the complementary groups of which are selected amongst the uracil, succinimide, thymine, glutarimide and cyanuric acid groups.

8. Monoacylaminopyridine Having the Structure (XIII):

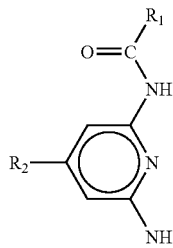

(XIII)

wherein:

R₁ and R₂ have the same meaning as previously defined, the -POL- polymeric backbone is attached in R₁ or R₂, and the complementary groups of which are selected amongst the uracil, succinimide, thymine, glutarimide and cyanuric acid groups.

9. 2,4-Diamino-s-triazinemonoacyl Having the Structure (XIV):

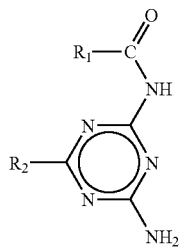

(XIV)

wherein:

R₁ and R₂ have the same meaning as previously defined, the -POL- polymeric backbone is attached in R₁ or R₂, and the complementary groups of which are selected amongst the uracil, succinimide, thymine, glutarimide and cyanuric acid groups.

10. Melamine with the Structure (XV):

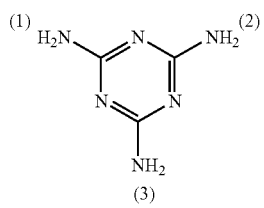

(XV)

wherein:
the -POL- polymeric backbone is attached in (1), (2) or (3) through reaction with one NH$_2$ pattern, and
the complementary groups of which are selected amongst the uracil, succinimide, thymine, glutarimide and cyanuric acid groups.

Preferably, the binding groups according to the invention are adapted to create at least four H links with an identical partner binding group.

Examples of binding groups adapted to create at least four H links with themselves include:
ureidopyrimidone;
2,4-diamino-3-triazine-bis-acyl,
ureidotriazine;
phthalhydrazide;
Urazoylbenzoic acid;

-POL- Polymeric Backbone

The polymeric backbones according to the invention may have any chemical nature and should have at least two repeating patterns.

They may be obtained through all techniques of polymerization (radical, ionic, group transfer, Ziegler or metallocene catalysis, etc. for those resulting from the polymerisation of unsaturated monomers) or polycondensation. They can result from natural occurring or chemically modified naturally occurring derivates.

The amount of repeating patterns or polymerisation degree of the polymeric backbone according to the invention generally ranges from 2 to 100.

Preferably, the polymerisation degree ranges from 10 to 500, so as to avoid the crystallisation of the polymer according to the invention and to make it possible that the composition according to the invention have film forming properties after application.

Preferably, the -POL- polymeric backbones do not carry any other groups adapted to create H links with the binding groups (A). Stated otherwise, they do not carry any groups adapted to be competitive with the binding groups (A) for creating H links, this in order to avoid hindering or weakening the formation of the supramolecular polymer.

Examples of polymeric backbones according to the invention include advantageously polydienes, polyesters, polycarbonates, polyacetals, polyoxyalkylenes, polythioethers, perfluoropolyethers, polyolefins, polyorganosiloxanes, vinyl polymers, poly(meth)acrylics, cellulosic derivates, polysaccharide derivates, including the ethers and esters.

For covalently attaching the binding groups (A) onto the -POL- polymeric backbones, one will preferably start from -POL- moieties carrying at least two reactive functional groups X carrying labile hydrogens, X representing —OH, —NH$_2$, —NHR, —SH, etc.

It is to be mentioned in particular:

1. Polydienes, Being Preferably Hydrogenated, with Hydroxy Ends and Polyolefins with Hydroxy Ends Polydienes, being preferably hydrogenated, with hydroxyl ends and polyolefins with hydroxy ends are the preferred polymeric backbones according to the invention.

Such hydroxy ended polydienes are defined for example in Patent FR 2 782 723 from ELF ATOCHEM. They are selected in the group comprising homo- and copolymers of polybutadiene, polyisoprene and poly(1,3-pentadiene). These are oligomers with a number average molecular mass lower than 7000, and preferably ranging from 1000 to 5000, having a functionality at the hydroxy ends from 1.8 to 3 and preferably close to 2.

Such polydienes are preferably used hydrogenated.

One can more particularly mention the hydroxylated polybutadiened sold by the ELF ATOCHEM corporation under the trademarks POLY BD R-45HT® and POLY BD R-20 LM®, which will be preferably used hydrogenated.

One can also use polyolefins, homopolymers or copolymers, with α,ω hydroxy ends such as:
oligomers of polyisobutylene with α,ω hydroxy ends;
copolymers sold by the Mitsubishi corporation under the trademark POLYTAIL® with, in particular, those having the formula (XVI):

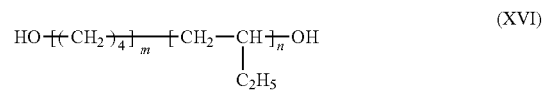

(XVI)

2. Polyesters Being Initially with α,ω-OH Ends

Polyesters initially with α,ω-OH ends, also called polyester-polyols, are also preferred -POL- polymeric backbones according to the invention.

The polyester-polyols according to the invention may be obtained through a reaction between
at least one polyhydric alcohol, selected amongst ethylene glycol, propylene glycol, diethylene glycol, neopentyl glycol, 1,4-butanediol, furane dimethanol, cyclohexane dimethanol, glycerol, trimethylpropane, pentaerythritol and the mixtures thereof, and
at least one polycarboxylic acid, preferably a dicarboxylic acid, or a derivate, including a diester, selected amongst succinic, glutamic, adipic acids and their dimethyl esters, and phthalic anhydride.

The polyester-polyol according to the invention may also be obtained through polymerisation of a lactone, for example caprolactone, and a polyol.

However, the preferred polyester-polyols according to the invention are polyester-polyols obtained through condensation with a dimeric fatty acid and/or a dimer-diol, as well as the polyester-polyols obtained through reaction with natural occurring or synthetic hydrocarbon oils carrying two to three hydroxy or epoxy groups.

2.1. Polyester-polyol Obtained Through a Condensation with a Dimeric Fatty Acid and/or a Dimer-Diol The dimeric fatty acids are defined in U.S. Pat. No. 5,998,570, U.S. Pat. No. 3,157,681 and U.S. Pat. No. 5,411,729, respectively of the formulae (XVII), (XVIII) and (XIX):

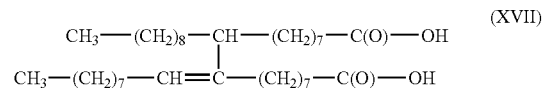

(XVII)

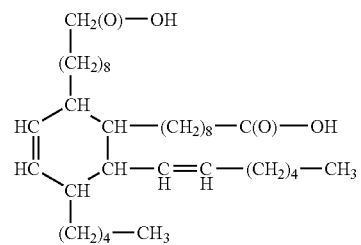

(XVIII)

-continued

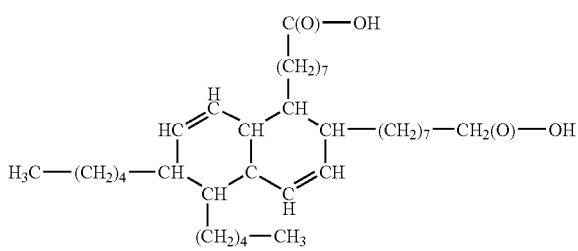
(XIX)

They are more particularly sold under the trade names: UNIDYME® by the UNION CAMP corporation, and PRIPOL® (for example PRIPOL 1013) by the UNICHEMA corporation.

The dimer-diols are those defined in the article by R. HÖFER, European Coating Journal, March 2000, pp. 26-37. They have the same chemical structures as the corresponding dimeric fatty acids, only the functionalities change.

As indicated in the article by R. HÖFER, European Coating Journal, March 2000, pp. 26-37, converting dimeric fatty acids into dimer-diols may occur:

either through an hydrogenation of methyl esters of the dimeric fatty acids, or through a direct dimerization of oleic alcohol.

One can particularly mention the dimer-diols sold by the COGNIS corporation under the trade names SOVERMOL 908® (with a dimer purity of 97.5%) and SOVERMOL 650 NS® (with a dimer purity of 68%).

2.2. Polyester-polyol Obtained Through a Reaction with Natural Occurring or Synthetic Hydrocarbon Oils Carrying from Two to Three Hydroxy (or Epoxy) Groups The preferred oils are obviously oils carrying two hydroxy groups per chain such as the monoglycerides of the structure (XX) or (XXI):

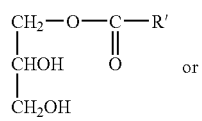
(XX)

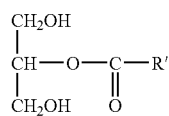
(XXI)

wherein R' is a linear or branched alkyl chain, such as for example glycerol monostearate.

Such glycerol monoesters correspond for example to the compounds:

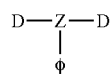

wherein:

D represents —O—, and

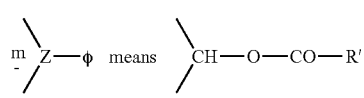

One can also mention naturally occurring oils (Vernonia) or synthetic oils comprising epoxy groups.

3. Polycarbonates Initially with α,ω-OH Ends

The polymeric backbones according to the invention may also be advantageously selected amongst polycarbonates with α,ω-OH ends.

The polycarbonates with α,ω-OH ends may be obtained through a reaction between a diol which may be selected amongst 1,3-propanediol, 1,4-butanediol, 1,6-hexanediol, diethyene glycol, and tetraethylene glycol, and a diarylcarbonate such as for example a diphenylcarbonate, or phosgene.

4. Polyalkylene oxides Initially with α,ω-OH Ends

As a polymeric backbone according to the invention, one can advantageously use polyalkylene oxides with α,ω-OH ends.

The polyalkylene oxides according to the invention may be obtained through polymerisation of cyclic oxides, particularly selected amongst ethylene oxide, propylene oxide and tetrahydrofuran, or through the addition of one or more cyclic oxides to polyfunctional initiators, more particularly selected amongst water, ethylene glycol, diethylene glycol, cyclohexane diethanol, glycerol, trimethylolpropane, pentaerythritol, and bisphenol A.

The polyoxypropylene diols and triols, poly(oxyethylene-oxopropylene) diols and triols, obtained through the simultaneous or sequential addition of ethylene oxides or propylene glycols to appropriate initiators, are the preferred polyalkylene oxides according to the invention.

Similarly, the polytetramethylene glycols obtained through polymerisation of tetrahydrofuran; and the polyalkylene oxides oligomers carrying at least two amine groups at the ends of the POE chain are particularly preferred polyalkylene oxides according to the invention.

One will also mention polyalkylene oxide oligomers carrying at least two amine groups at the ends of the POE chain, such as diamines of polyalkylene oxides JEFFAMINE® commercialised by the TEXACO corporation.

5. Polythioethers Initially with α,ω-OH Ends

It is also possible to use as the polymeric backbone according to the invention a polythioether with an α,ω-OH end.

The polythioethers used according to the invention may be obtained through condensation of the thiodiglycol alone or with other glycols, or dicarboxylic acids, formaldehyde, aminoalcohols or aminocarboxylic acids.

6. Polyacetals Initially with α,ω-OH Ends

One may also use a polymeric backbone selected amongst the polyacetals initially with an α,ω-OH end.

Polyacetals useful according to the invention may include the polyacetals obtained trough reaction between at least one glycol, particularly selected amongst diethylene glycol, trimethylene glycol and hexanediol, and formaldehyde.

One can also use polyacetals obtained through polymerisation of cyclic acetals.

7. Polyorganosiloxanes Initially Carrying at Least Two Reactive Groups Such as —OH, —NH$_2$, —NHR, —SH, and

The polyorganosiloxanes initially carrying at least two reactive groups selected amongst the —OH, —NH$_2$, —NHR groups (where R is such as previously defined), —SH, and

are also polymeric backbones useful according to the invention.

According to a particular embodiment of the invention, one will use an α,ω-telechelic polyorganosiloxane with —OH, —NH$_2$ and —NHR ends, having the structure (XXII):

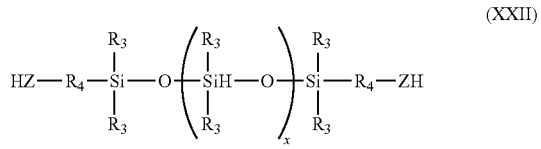

wherein:
  x represents an integer from 0 to 100,
  Z represents —O—, or —NH— or —NR—,
  R is such as previously defined,
  $R_3$ is a group selected amongst $C_1$-$C_{40}$ linear or branched alkyl or alkoxy chains (with preferably —CH$_3$, —C$_2$H$_5$, n-C$_3$H$_7$ and iso-C$_3$H$_7$), the phenyl groups, optionally substituted by from 1 to 3 methyl or ethyl groups, the polyorganosiloxane chains, the $C_1$-$C_{12}$ linear or branched fluoroalkyl groups and the $C_1$-$C_{12}$ linear or branched fluoroalkoxyethylene groups,
  $R^4$ is selected amongst $C_1$-$C_{60}$ divalent alkyl groups, $C_1$-$C_{60}$ oxyalkylene groups and containing from 0 to 3 ethylene oxide patterns, and the mixtures thereof, and wherein each atom directly linked to a hydroxy group is a carbon atom.

One will preferably use polyorganosiloxanes where $R_4$ is a $C_1$-$C_{10}$ alkylene divalent moiety wherein x is an integer such that the number average molecular mass of the polysiloxane ranges from 300 to 10000.

More preferably, one will use polydimethylsiloxanes having the structure (XXIII):

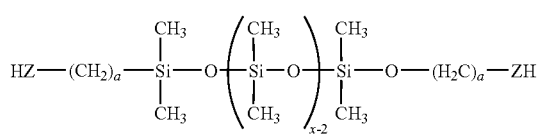

wherein:
  a represents an integer ranging from 1 to 10, and
  Z is such as defined hereinabove.

Such α,ω functional oligomers are more particularly commercialised by the GOLDSCHMIDT corporation under the trade names:

TEGOMER H—Si 2111® with x being such that the number average molecular weight PM is 700 (with Z representing —O—), TEGOMER H—Si 2311® with x being such that the number average molecular weight PM is 2,200 (with Z representing —O—), TEGOMER A-Si 2122® with x=10 (with Z representing —R—NH(R')).

Examples of α,ω difunctional oligomers also include those oligomers commercialised by the SHIN-ETSU corporation under the trade names:
  X-22-161AS®, X-22-161A®, X-22-161B®, X-22-161C® (with Z representing —NH—),
  X-22-160AS®, KF-6001®, KF-6002®, KF-6003® and x-22-4015® (with Z representing —O—).

Examples of preferred α,ω-telechelic polyorganosiloxanes also include polyorganosiloxanes wherein $R_4$ is advantageously an oxyalkylene group, comprising butylene oxide patterns or propylene oxide patterns, or from 0 to 3 ethylene oxide patterns.

One will preferably use those polyorganosiloxanes with the structure (XXIV):

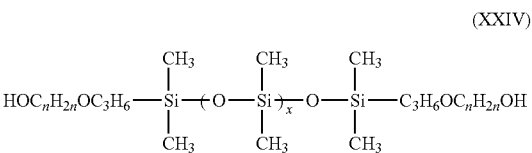

wherein:
  n varies from 2 to 6 independently, et
  x is an integer from 2 to 100.

As examples of such polyorganosiloxanes, one can mention more particularly those polyorganosiloxanes with the structure (XXV):

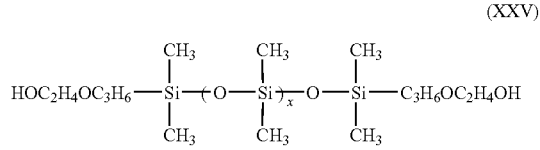

wherein x is an integer from 2 to 100.

Such polyorganosiloxanes are commercialised under the trade name SILAPLANE FM-4425 by the CHISSO AMERICA, Inc. corporation.

According to another embodiment of the invention, one will use polyorganosiloxanes with polyalkylene oxide grafts ending with —OH groups (POE grafts or POE-PPO grafts: usual dimethicone copolyols), of a structure represented by the formula (XXVI):

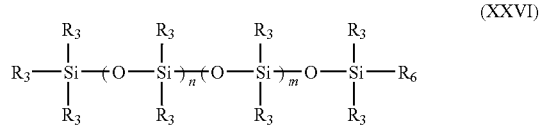

wherein:
  $R_3$ has the same meaning as in formula (XXII);
  $R_5$ is a monovalent polyalkylene oxide group with a —OH end,
  $R_6$ is identical to $R_3$ or $R_5$.

According to a third embodiment of the invention, one will use polyorganosiloxanes with side and/or end amine groups, having the structure represented by the formula (XXVII):

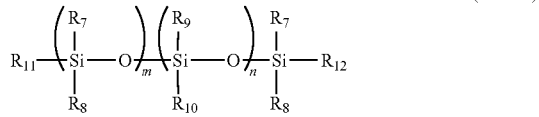
(XXVII)

wherein:
the groups represented by the $R_7$ and $R_9$ symbols may be identical or different, and are selected amongst alkyl groups comprising from 1 to 22 carbon and phenyl, naphthyl or polyoxyalkylene groups, at least one of the groups represented by the $R_{10}$ and $R_{12}$ symbols is a group of the structure $H_2N\text{---}(\text{---}R_{13}\text{---}NH\text{---})_s\text{---}R_{14}$, where $R_{13}$ and $R_{14}$ each represent an alkylene group comprising from 1 to 6 carbon atoms and s is 0 or 1, the other groups may be identical or different, and are alkyl groups comprising from 1 to 22 carbon atoms, or phenyl groups, or naphthyl groups or polyoxyalkylene groups, and m and n each represent a number equal to at least 1.

According to a fourth embodiment, polyorganosiloxanes with side and/or end thiol-SH groups will be used.

According to a fifth embodiment, polyorganosiloxanes with side and/or end hydrogenosilane groups will be used having the general structure represented by formula (XXVIII) or (XXIX):

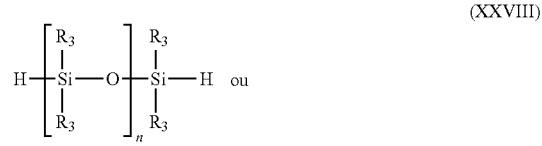
(XXVIII)

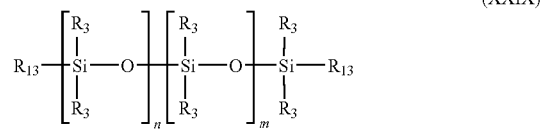
(XXIX)

wherein:
$R_3$ is such as previously defined (XXII);
$R_{13}$ represents either $R_3$ or H.

Such polyorganosiloxanes can only be used for attachment of binding groups (A) carrying a double (met)allyl link.

As examples of such polyorganosiloxanes, one can mention polyorganosiloxanes with side and/or end hydrogenosilane groups commercialised by the ABCR corporation.

8. Perfluoropolyethers Initially with α,ω-OH Ends

The polymeric backbones according to the invention may also be advantageously selected amongst perfluoropolyethers with side and/or end hydroxyl groups, and preferably the perfluoropolyetherdiols of the structure represented by formula (XXX):

HO-Q-Rf—O—$(C_iF_{2i}O)_j$—$(C_yF_{2y}O)_k$—$(C_zF_{2z}O)_p$—Rf-Q'-OH  (XXX)

wherein:
the —$(C_iF_{2i}O)$—, —$(C_yF_{2y}O)$— and —$(C_zF_{2z}O)$— oxyperfluoroalkylene groups are randomly distributed, or are grouped as a block in one chain;
i is an integer from 1 to 10,
j is an integer from 0 to 100,
k is an integer from 1 to 100,
p is an integer from 0 to 100,
y is an integer from 1 to 10,
z is an integer from 1 to 10,
each Rf group is independently selected amongst the divalent perfluoroalkyl moieties comprising from 1 to 20 carbon atoms,
each group Q is independently selected amongst the —$C_6H_4$—, —$C_6H_3Cl$—, —$C_2H_4OCH_2$— and —$C_bH_{2b}$— groups, and
each group Q' is independently selected amongst the —$C_6H_4$—, —$C_6H_3Cl$—, —$C_2H_4OCH_2$— and —$C_bH_{2b}$— groups, and
b is an integer from 1 to 20.

Such perfluoroether-diols are for example those defined in the International Patent Application WO 98/44015 and in the article by T. TEMTCHENKO et al., XXVIth International Conference in Organic Coatings, 3-7 Jul. 2000, VOULIAG-MENI (ATHENS), Book of Conf., pp. 357-65.

They are commercialised by the AUSIMONT corporation under the trade names:
FLUOROBASE Z 1030, corresponding to k=j=6;
FLUOROBASE Z, corresponding to a k/j ratio=¼ and a number average molecular weight (PM) from 1000 to 4000, and preferably from 500 to 700, with more particularly an OH weight percentage ranging from 4.8 to 6.8%;
FOMBLIN HC/OH 1000, with a number average molecular weight equal to 1036, with a hydroxy end functionality equal to 2, and with a structure represented by the formula (XXXI):

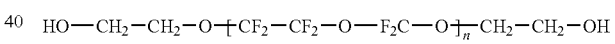
(XXXI)

9. Vinyl or (meth)acrylic oligomers or polymers Initially with —OH, —$NH_2$, —NHR, —SH reactive groups According to the invention, it is also possible to use as a polymeric backbone vinyl or (meth)acrylic oligomers or polymers initially with —OH, —$NH_2$, —NHR reactive groups (where R is as previously defined), or —SH.

Such polymers are generally selected amongst homo- or copolymers with —OH, —$NH_2$, —NHR side groups (where R is such as previously defined).

These are preferably oligomers with a number average molecular weight of less than 10000, obtained through copolymerisation of one or more vinyl and allyl monomers, olefins, vinylether, (meth)acrylic acids or esters or amides, with at least one co-reactive monomer carrying at least one group selected amongst —OH, —$NH_2$ and —NHR.

Examples include homo- and copolymers obtained through polymerisation with:
a hydroxyalkyl(meth)acrylate, such as 2-hydroxyethyl acrylate, or
the vinyl alcohol (obtained through hydrolysis of the vinyl acetate patterns of the polymer), or
the allyl alcohol,
the vinylamine, or
the allylamine.

But it is also possible to use those (homo- and co-) oligomers carrying α,ω-OH reactive ends.

The polymerisation of methacrylic monomers (acids, esters or amides) in the presence of a 2-mercaptoethanol transfer agent (HS—CH$_2$—CH$_2$—OH) leads to functionalised oligomers at each α,ω end by a hydroxyethylsulfide group:

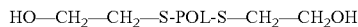

où POL désigne:

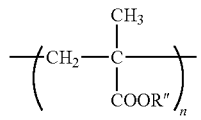

wherein R″ represents a group selected amongst the alkyl, aryl, aralkyl, alkenyl, alkoxy, alkoxyalkyl, alkoxyaryl or phenyl groups.

Such a polymerisation is disclosed in the article by G. REUSMANN, Eur Coat. J., 9, 52-53, 56, 58 (1999) and also N. KEBELKAMP A Farbe Lack, 105, (2), 24-26, 28-29 (1999) disclosing the synthesis of such α,ω-polymethacrylate-diols and their use for producing polyurethanes.

10. Cellulose Derivates

The POL polymeric backbone according to the invention may also be selected amongst cellulose derivates.

Amongst them, one can mention cellulose hydroxyalkylethers and alkylethers (or guar, etc.), cellulose esters (such as acetates, propionates, butyrates and mixed esters), and nitrocellulose.

11. Di- Tri-, Tetra- and More Generally Polysaccharides or the Derivates Thereof The POL polymeric backbone according to the invention may also be selected amongst di-, tri-, tetra- and more generally polysaccharides or the derivates thereof, in particular ethers and esters.

12. Hyperbranched or Dendrimers, Initially with Reactive Ends of the —OH, —NH$_2$, —NHR and —SH Type Finally, the POL polymeric backbone according to the invention may be selected amongst the hyperbranched or dendrimers, initially with reactive ends of the —OH, —NH$_2$, —NHR and —SH type.

The dendrimers (from the Greek dendron=tree) are "arborescent" polymeric molecules, i.e. highly branched, invented by D. A. Tomalia and its staff at the early nineties (Donald A. Tomalia and al., Angewandte Chemie, Int. Engl. Ed., vol 29, n° 2, pp. 238-175). These are molecular structures built around a generally polyvalent central pattern. Around said central pattern are chained, in concentric layers and according to a perfectly determined structure, chain extending branched patterns also giving rise to symmetrical monodispersed macromolecules with a well defined chemical and stereochemical structure. Polyaminoamine type dendrimers are commercialised for example under the trade name STARBUST® by the DENDRITECH corporation.

The hyperbranched polymers are polycondensates, generally of the polyester, polyamide or polyethyleneimine type, obtained from multifunctional monomers, which have an arborescent structure similar to that of dendrimers, but much less regular than the latter (see for example International Patent Applications WO-A-93/17060 and WO-96/12754).

The PERSTORP corporation sells under the trade name BOLTORN® hyperbranched polyesters. One will also find under the trade name COMBURST® from the DENDRITECH corporation hyperbranched polyethyleneimines and hyperbranched polyesteramides with hydroxy chain ends commercialised under the trade name HYBRANE® by the DSM corporation.

As previously indicated, after functionalisation of such dendrimers or hyperbranched polymers, with their ends being attached by binding groups -(A), they will be preferably used as a blend with other A-POL-A polymers according to the invention having only two groups (A) per molecule, so as to make cross-linked deposits, after application and drying of the cosmetic composition cosmetic.

Attachment of the Binding Groups (A) on the POL Polvmeric Backbone

The attachment chemical reactions mentioned herein are not limitative, but are only given by way of illustration.

According to a first embodiment of the invention, the binding groups are attached onto POL polymeric backbones comprising labile hydrogen groups such as —OH, —NH$_2$, —NHR (wherein R is such as previously defined) or —SH, via the functionalisation of the binding group (A) by an isocyanate. Such a reaction comprises the following steps of:

functionalizing the group A by an isocyanate according to the reaction scheme:

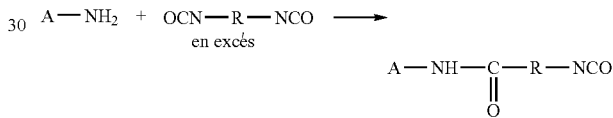

and then reacting with a POL polymeric backbone comprising at least two labile hydrogen groups such as —OH, —NH$_2$, or —SH.

As an example, one can mention the attachment reaction for an ureidopyrinidone group, such as for example 6-methylisocytosine, onto a POL polymeric backbone with a HO-POL-OH or H$_2$N-POL-NH$_2$ structure:

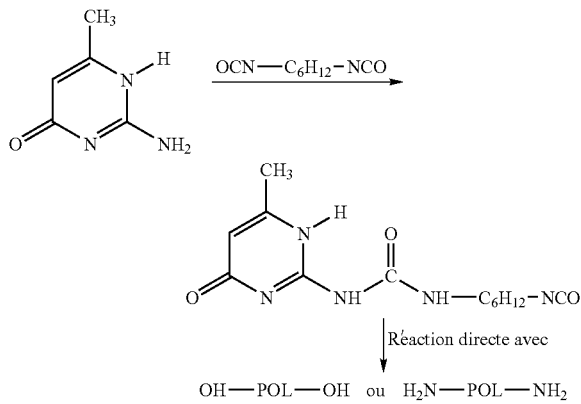

Such a reaction is described in further detail in the article by B. J. B. FOLMER, Adv. Mater, 12, 874-78 (2000).

It is also possible to perform the reverse reaction by pre-functionalising the polymeric backbone with a labile hydrogen group such as —OH, NH$_2$, —NHR (where R is such as previously defined) or —SH by a diisocyanate.

As an example, one can mention the reaction of a polymeric backbone POL with a following diisocyanate:

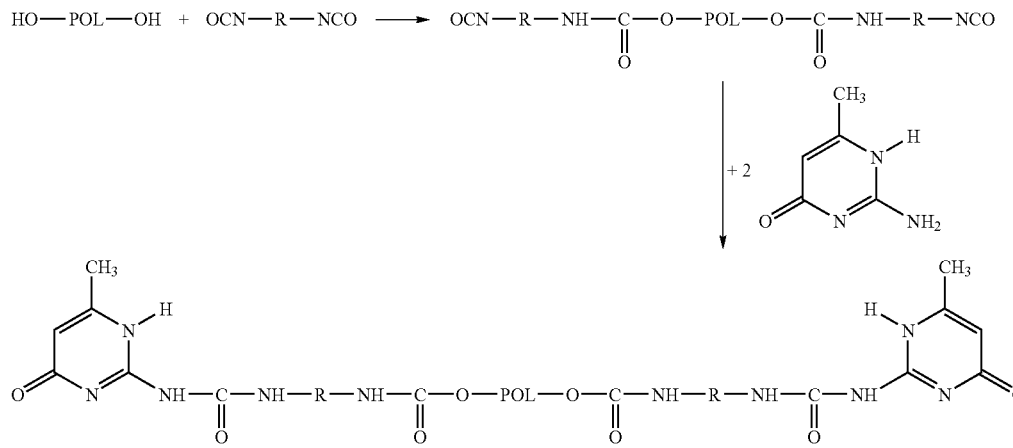

Such a reaction is also described in the article by B. J. B. FOLNER, Adv. Mater, 12, 874-78(2000). This article also indicates the attachment conditions of ureidopyridimidone groups, for either of the two pathways described hereinabove, on POL polymeric backbones of the following nature:

polyoxyalkylene (for example: HO—POE/PPO—OH), polyester (for example: butyl polyadipate with —OH end), polycarbonate (for example: hexyl polycarbonate) with α,ω-OH end), copoly(ethylene/butylene) with α,ω-OH ends.

Those two attachment pathways for the ureidopyrimidone groups may be transposed to all the -POL- polymeric backbones according to the invention comprising two or more —OH, —NH, —NHR, and —SH groups.

The attachment conditions for the 6-methylisocytosine groups, via the isophorone diisocyanate on POE/PPO block polymers with —OH ends are described in detail in the article by R. F. M. LANGE, J. Polymer Sci: Part A, Polym. Chem., 37, 3657-70 (1999) as well as in the International Patent Application WO 98/14504.

Alternatively, the binding groups (A) are attached onto the polyorganosiloxanes through hydrolyse. Such a reaction comprises the following steps of:

functionalizing (A) by an allyl —CH$_2$—CH═CH$_2$ group by direct synthesis→CH$_2$═CH—CH$_2$-(A);

and then reacting with an organosiloxane carrying two or more hydrogenosilane —S$_i$H groups as follows:

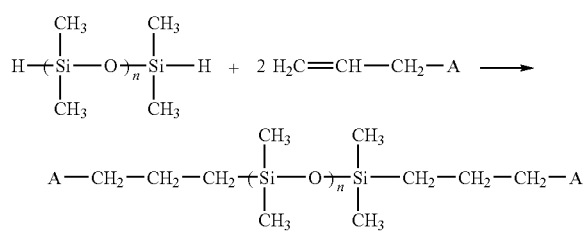

An example includes the hydrosilylation reaction described in the article by R. P. S. SIVBESMA, Science, 278, 1601-04 (1997):

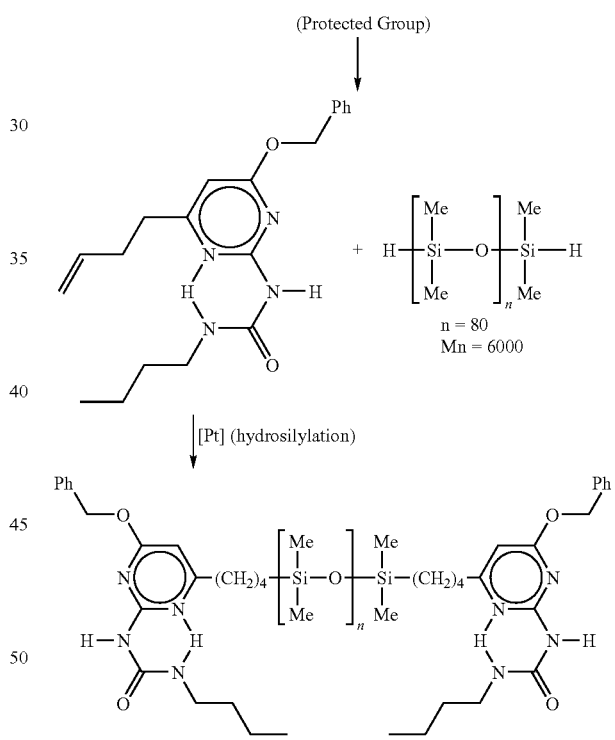

followed with the protection of phenyl groups through hydrogenation on palladium.

Such protection, hydrosilylation and then deprotection reactions are detailed in the article by J. H. K. K. HIRSCH-BERG, Macromolecules, 32, 2696-2705 (1999) and in the International Patent Publication WO-98/14504 from DSM.

Galenic Forms

The compositions useful in the invention may have any galenic forms conventionally used for a topic application and in particular, under the form of an aqueous, alcoholic or hydroalcoholic solution or suspension, or an oily solution or a lotion or serum type solution or dispersion, a milk-like liquid or semi-liquid consistency emulsion, obtained by dispersion of a fatty phase in an aqueous phase (H/E) or vice versa (E/H), or a suspension or emulsion with a soft consistency of the cream type (H/E) or (E/H), or an aqueous or anhydrous gel, an ointment or any other galenic form.

The compositions according to the invention generally comprise a physiologically acceptable medium, i.e. compatible with cutaneous tissues such as skin and keratin materials.

The physiologically acceptable medium is advantageously a medium that is not detrimental to the properties of an increased persistence of at least one cosmetic and/or care effect, an adhesion on keratin materials and an easy make-up removal provides by the composition after application.

Preferably, the physiologically acceptable medium is a solubilising medium for the polymers according to the invention comprising at least one solvent.

Solvents useful according to the invention include water, alcohols and preferably short alcohols, polyols, short esters, hydrocarbon oils, silicone oils, fluorinated silicone oils and the mixtures thereof. The oils may be polar or apolar.

Amongst those solvents, one can mention as an example the $C_1$-$C_4$ lower alkanols such as ethanol and isopropanol, polyols, glycol ethers, such as 2-butoxyethanol, ethylene glycol, glycerin, propylene glycol, diethylene glycol monoethylether and monomethylether, as well as aromatic alcohols such as benzyl alcohol or phenoxyethanol and similar products or the mixtures thereof.

Polar oils include hydrocarbon oils comprising ester, ether, acid, alcohol functions or the mixtures thereof, such as for example:

hydrocarbon vegetable oils with a high triglyceride content consisting in esters of fatty acids and glycerol where the fatty acids may have variable chain lengths, the latter being linear or branched, saturated or unsaturated; with such oils being particularly wheatgerm, corn, sunflower, karite, castor, sweet almond, macadamia, apricot, soja, rapeseed, cotton, alfalfa, poppy, potimarron, sesame, marrow, avocado, hazelnut, grape or blackcurrant seeds, onager, millet, barley, quinoa, olive, rye, carthame, candlenut, passiflora and Muscat rose-tree oils; or also caprylic/capric acid triglycerides such as those sold by the Stearineries Dubois corporation or those sold under the trade names Miglyol 810, 812 and 818 by the Dynamit Nobel corporation;

synthetic oils of the formula $R^1COOR^2$ wherein $R^1$ represents the remainder of a linear or branched higher fatty acid comprising from 7 to 19 carbon atoms, and $R^2$ represents a branched hydrocarbon chain containing from 3 to 20 carbon atoms, such as for example the Purcellin oil (cetostearyl octanoate), isononyl isononanoate, $C_{12}$-$C_{15}$ alkyl benzoates;

synthetic esters and ethers such as isopropyl myristate, ethyl-2-hexyl palmitate, octanoates, decanoates or ricinoleates of alcohols or polyalcohols;

hydroxy esters such as isostearyle lactate, di-isostearyl malate and pentaérythritol esters;

$C_8$ à $C_{26}$ fatty alcohols such as oleic alcohol; and the mixtures thereof.

The apolar oils include:

volatile or not, linear or cyclic, silicone oils being liquid at room temperature, such as polydimethylsiloxanes (PDMS) comprising alkyl, alkoxy or phenyl groups, either pendant and/or at the end of the silicone chain and having from 2 to 24 carbon atoms; phenyl silicones, such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates;

hydrocarbons or fluorinated hydrocarbons and/or fluorocarbons, either linear or branched, from a synthetic or mineral origin, such as volatile oils, like paraffin oils (for example isoparaffins), and aliphatic hydrocarbons (for example isododecane), or not volatile oils and the derivates thereof, petroleum jelly, polydecenes, hydrogenated polyisobutene such as parleam, squalane and the mixtures thereof.

The solvents are preferably present in proportions ranging from 1 to 90% in weight, and in particular from 5 to 70% in weight based on the total weight of the composition.

The solubility of the polymers according to the invention will be controlled by the selection of the -POL- polymeric backbones and binding groups (A).

The polymers of the invention may in some cases already interact between themselves physically (creating a network of H interactions) in some solvents or mixtures of solvents. This depends upon the nature and proportions of solvents or mixtures of solvents being used. This can lead to an unwanted increase of the viscosity of the formula and hinder its application (for example a lotion, an aerosol, etc.).

To overcome such a viscosity problem, one can operate in two ways:

either solubilizing the polymer according to the invention in a volatile solvent adapted to create H interactions H with binding groups (A) of the polymers, for example using short alcohols, volatile polyols and water, or using a diphasic solubilizing medium, as for example a water-in-oil (E/H) or oil-in-water (H/E) emulsion and a couple of selective polymers according to the invention with their binding groups and their polymeric backbones being of different chemical natures, each polymer being dissolved in a phase differing from the other (one in water, the other one in oil).

The couple of A-$POL_1$-A and B-$POL_2$-B polymers is then selected so that:

each of the binding groups (A) does not create any H interaction with itself, but only with (B), each of the binding groups (B) does not create any H interaction with itself, but only with (A), the binding groups (A) and (B) create H interactions only when they come into contact together, and the -$POL_1$- and -$POL_2$- polymer backbones are selected so that the A-$POL_1$-A and B-$POL_2$-B polymers may each be carried in a distinct phase of the emulsion, so that they cannot react in the emulsion.

The interaction between both polymers will only occur upon application, on the condition however that the solubilizing media should be volatile solvents or can penetrate into the keratin support.

As is known, the composition of the invention may also contain the usual builders common in the cosmetic and dermatological fields as long as the builder does not alter the properties looked for the composition of the invention, such as hydrophilic or lipophilic gellants, hydrophilic or lipophilic care active ingredients, preservatives, antioxidants, perfumes, fillers, neutralizing agents, other polymers than those previously defined, emulsifiers and co-emulsifiers.

The amounts of those various builders are those conventionally used in the subject fields, and for example, ranging from 0.01 to 30% of the total weight of the composition. Such builders, depending upon their nature, may be introduced into the fatty phase, the aqueous phase, the lipidic vesicles and/or the nanoparticles.

The emulsifiers and co-emulsifiers optionally used in the composition under the form of an emulsion are selected depending on the emulsion type (E/H or H/E) amongst those conventionally used in the subject field.

Such emulsifiers and co-emulsifiers are preferably present in the composition in a proportion ranging from 0.3 to 30% in weight, and preferably from 0.5 to 20% in weight based on the total weight of the composition.

Emulsifiers and co-emulsifiers useful in the invention include for example esters of fatty acids and polyols such as PEG-100 stearate, PEG-50 stearate and PEG-40 stearate; sorbitan tristearate, oxyethylenated sorbitan stearates comprising for example 20 to 100 EO, and for example those available under the trade names Tween® 20 or Tween® 60 and the mixtures thereof, such as the mixture of glyceryl monostearate and polyethylene glycol stearate (100 EO) commercialized under the trade name SIMULSOL 165® by the SEPPIC corporation.

Silicone emulsifiers can be also mentioned such as dimethicone copolyols and alkyl dimethicone copolyols. One can mention for example as dimethicone copolyol, the mixture of dimethicone copolyol, cyclomethicone and water (10/88/2), commercialized by the Dow Corning corporation under the trade name DC3225C® or DC2-5225C®, and as alkyl dimethicone copolyol, those having an alkyl moiety comprising from 10 to 22 carbon atoms, such as cetyl dimethicone copolyol like the product commercialized under the trade name Abil EM-90® by the Goldschmidt corporation and the mixture of dimethicone copolyol and cyclopentasiloxane (85/15) commercialized under the trade name Abil EM-97® by the Goldschmidt corporation; lauryl dimethicone copolyol and for example the mixture of approximately 91% lauryl dimethicone copolyol and approximately 9% isostearylic alcohol, commercialized under the trade name Q2-5200® by the Dow Corning corporation, and the mixtures thereof.

As hydrophilic gellants, one can more particularly mention carboxyvinylic polymers (carbomer), acrylic copolymers such as acrylate/alkylacrylate copolymers, polyacrylamides, polysaccharides, natural occurring gums and clays.

As lipophilic gellants, one can mention modified clays such as bentones, metal salts of fatty acids and hydrophobic silica.

As care active ingredients, one can use in particular depigmenting agents, emollients, moisturising agents, antiseborrheic agents, anti-acne agents, hair growth promoting agents, keratolytic and/or desquamative agents, antiwrinkle and tensor agents, anti-irritating agents, soothing agents, vitamins, screens, odour absorbers and the mixtures thereof.

Of course, the man of the art will take care to select the possible compound(s) to be added to the compositions according to the invention, as well as the concentration thereof, so that the advantageous properties intrinsically associated with the compositions according to the invention are not or substantially not altered by the contemplated addition.

The composition according to the invention may take the form of a care composition, particularly a moisturising one, for keratin materials such as skin, lips and/or dermoskeleton and/or the form of a body hygiene composition, in particular the form of a deodorant or make-up removal product, or the form of a make-up product for the keratin materials, and/or the form of a cleansing product and/or the form of a hair product, for example a shampoo or a hair conditioner or also a hairstyling product.

Advantageously, the composition contains at least one colouring material. Such a colouring material may comprise from 0.01 to 50% in weight, preferably from 0.5 to 40% in weight based on the total weight of the composition.

As colouring material useful according to the invention, one can mention lipophilic dyes, hydrophilic dyes, pigments and pearlescent products usually used in cosmetic or dermatologic compositions, and the mixtures thereof.

Fat-soluble dyes are, for example, Sudan red, DC Red 17, 1 DC Green 6, carotene, soja oil, Sudan brown, DC Yellow 11, DC Violet 2, DC orange 5, quinoline yellow and annatto. They can comprise from 0.01 to 10% of the weight of the composition, and preferably from 0.05 to 5%.

The pigments may be white or coloured, mineral or/and organic, coated or not.

Mineral pigments include titanium dioxide, optionally surface treated, zirconia or ceria, as well as iron or chromium oxides, manganese violet, ultramarine blue, chromium hydrate and ferric blue.

The preferred mineral pigments are iron oxides, including red iron oxide, yellow iron oxide, red and yellow iron oxide, brown iron oxide, black iron oxide and titanium dioxide.

The organic pigments include:
carbon black,
pigments of the D&C type, such as D&C Red No 36, and
lacquers based on cochineal carmine, barium, strontium, calcium such as D&C Red No 7 calcium lake, aluminium such as D&C Red No 27 aluminium lake, D&C Red No 21 aluminium lake, FD&C Yellow No 5 aluminium lake, FD&C Yellow No 6 aluminium lake, D&C Red No 7 and FD&D Blue No 1.

The pigments can comprise from 0.01 to 40% of the total weight of the composition, and preferably from 1 to 30%.

The pearlescent pigments can be selected amongst white pearlescent pigments, such as mica coated with titanium or bismuth oxichloride, coloured pearlescent pigments such as mica titanium with iron oxides, mica titanium with particularly ferric blue or chromium oxide, mica titanium with an organic pigment of the above-mentioned type, as well as pearlescent pigments based on bismuth oxichloride. They can comprise from 0.01 to 40% of the total weight of the composition and preferably from 0.1 to 30%.

The composition of the invention may take the form of a skin make-up product, in particular a coloured one, especially a foundation cream, optionally having care properties, a blusher, a cheek or eyelid make-up product, an eye shadows concealer, an eyeliner; a lip make-up product such as a lipstick, optionally having care properties, a lip gloss, a lip pencil; a make-up product for the dermoskeleton such as nails, eye-lashes in particular in the form of a mascara bar, eye-brows and hair in the form of a pencil; a temporary tattoo product for the body skin.

The composition preferably has the form of a coloured product for lips.

The composition of the invention may also have the form of a hair colouring product.

It may also have the form of a non coloured care product adapted for treating skin and especially for moisturizing it, smoothing it out, depigmenting it, feeding it, protecting it from the sun rays or for providing it with a specific treatment. To this end, it advantageously contains at least one care active ingredient selected amongst depigmenting agents, emollients, moisturizing agents, antiseborrheic agents, anti-acne agents, hair growth promoting agents, keratolytic and/or desquamative agents, antiwrinkle and tensor agents, anti-irritating agents, soothing agents, vitamins, screens, odour absorbers and the mixtures thereof.

Another object of the invention is also a method for improving at the same time the persistence of at least one effect provided after deposition by a cosmetic composition and the adhesion of the composition applied on keratin materials, and also for allowing a quick, complete and selective removal of the deposition, consisting in adding to the composition an efficient amount of at least one linear, branched or cyclic polymer, or dendrimer, comprising:
- POL - polymeric backbone comprising at least two repeating patterns, and
- at least two binding groups (A), either identical or different, either lateral in the chain or terminal, attached onto the polymeric backbone and adapted to create at least three H links with one or more partner binding groups, of an identical or different chemical nature, each coupling of two binding groups (A) involving interfering at least three H links.

The deposit removal may consist, among others, in rinsing out a cleansing composition or in removing the make-up deposit (including lipstick, foundation cream, mascara, eyeliner).

Another object of the invention is also the use such as defined according to claim 22.

The invention is further detailed in the following examples. The amounts are given in mass percentage.

EXAMPLES

Example 1

Production of a Bifunctional POE/PPO Copolymer Having Three Ureidopyrimidone Ends The synthesis of the trifunctional POE/PPO copolymer is altogether identical to that described in the article by R. F. M. LANGE, J. Polym. Sci.: Part A=Polym. Chem., 37, 3657-70 (1999).

Reactive Agents
Compound 1
A POE/PPO copolymer with three OH ends, having a structure of the formula (XXXII):

wherein x and y are such that the number average molecular weight is 600, commercialized by the ARCO corporation.

Compound 2

An isopherone diisocyanate commercialized by the BAYER corporation, having the structure:

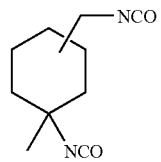

Compound 3
A methyl isocytosine:

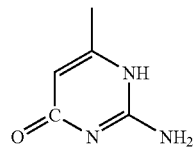

commercialized by the FLUKA corporation.
Solvent: $CHCl_3$
Pyridine

Operating Mode

A catalytic amount (about 30 mg) of $Ti(OnBu)_y$ is added to a solution containing 25.4 g (i.e. 5.3 mmol) of compound 1 in 50 ml $CHCl_3$ and the mixture is stirred for 10 minutes. Then 3.24 g (i.e. 16.7 mmol) of compound 2 are added dropwise and the mixture is stirred for 14 hours at room temperature. Infrared analyses (IR) of the reaction mixture show that there is no more free hydroxy functions of compound 1. The solvent is removed through evaporation under reduced pressure.

Then, 50 ml of pyridine and 2.25 g (i.e. 18.0 mmol) of compound 3 are added to the reaction mixture and the reaction mixture is allowed to react at reflux for 18 hours. IR analyses show that there are no more free isocyanate groups. The solvent is removed (pyridine) through vacuum evaporation. The raw reaction product is dissolved in $CHCl_3$, filtrated, then precipitated in n-hexane, and finally purified by filtration through a thin layer of silica: then 28.5 g of POE/PPO copolymer are obtained with three ureidopyrimidone ends with a reaction yield of 95%.

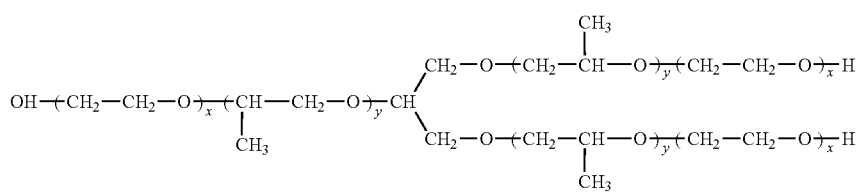

Example 2

Preparation of a polydimethylsiloxane (n=80) Having Two Ureidopyrimidone Ends The synthesis of such a compound is altogether identical to those described in the article by J. H. K. K. HIRSCHBERG, Macromolecular, 32, 2696-2705, (1999), and in the International Patent Application WO 98/14504 (examples 9, 10 and 13, on pp. 18, 19 and 22, respectively).

The synthesis will be presented herein as mentioned in the article by HIRSCHBERG, conducted with a polyhydrogenoorgano-siloxane (n=80) so as to give the final product 1: n=100. The synthesis of the polydimethyl siloxane with two ureidopyrimidone ends comprises four steps:

- the first step consists in preparing 6-(3-butenyl)isocytosine (compound 4), as shown in scheme 1,
- the second step consists in preparing 4-benzyloxy-6-(3-butenyl)-2-butylglureidopyrimidone (compound 6), as shown in scheme 2,
- the third step consists in preparing α,ω-di(4-benzyloxy-6-butyl-2-butylureidopyrimidinyl)poly(dimethylsiloxane) (compound 2-Bn), as shown in scheme 3, and
- the fourth step consists in preparing polydimethylsiloxane (compound 2), as shown in scheme 4.

Compound 2
α,ω-di(6-butyl-2-butylureido-4-pyrimidinoyl)poly(dimethylsiloxane)

Compound 2-Bn
α,ω-di(4-benzyloxy-6-butyl-2-butylureidopyrimidinyl)poly(dimethyl-siloxane)

Compound 3
Ethyl 3-oxo-6-heptenoate

Compound 4
6-(3-butenyl)isocytosine

Compound 5
6-(3-butenyl)-2-butylureido-4-pyrimidinone

Compound 6
4-benzyloxy-6-(3-butenyl)-2-butylureidopyrimidine

Synthesis of 6-(3-butenyl)isocytosine (Compound 4)

Scheme 2

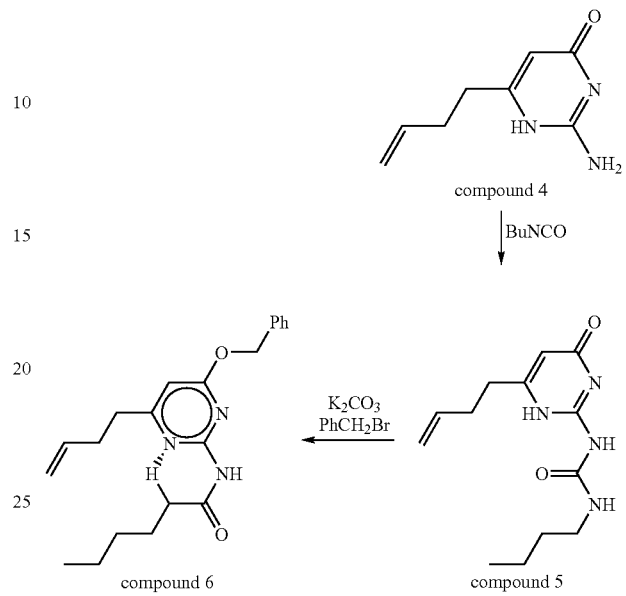

Synthesis of 4-benzyloxy-6-(3-butenyl)-2-butylureidopyrimidine (Compound 6)

Scheme 3

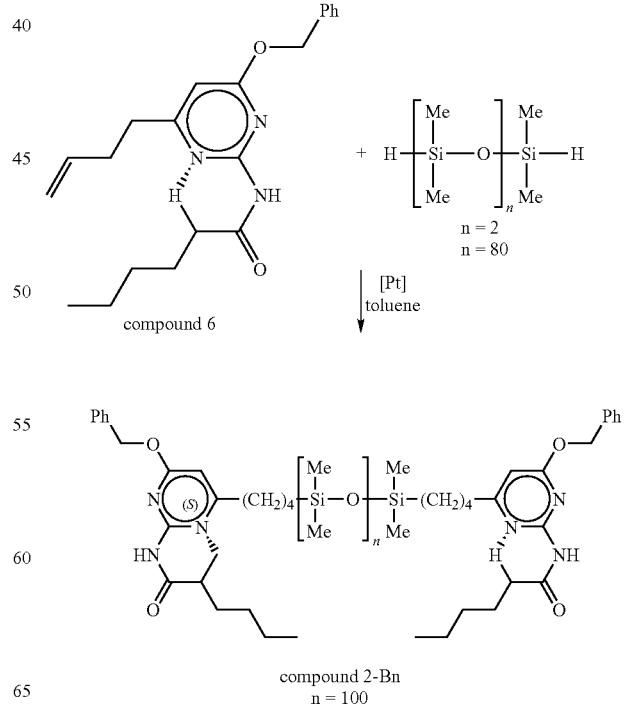

Scheme 1

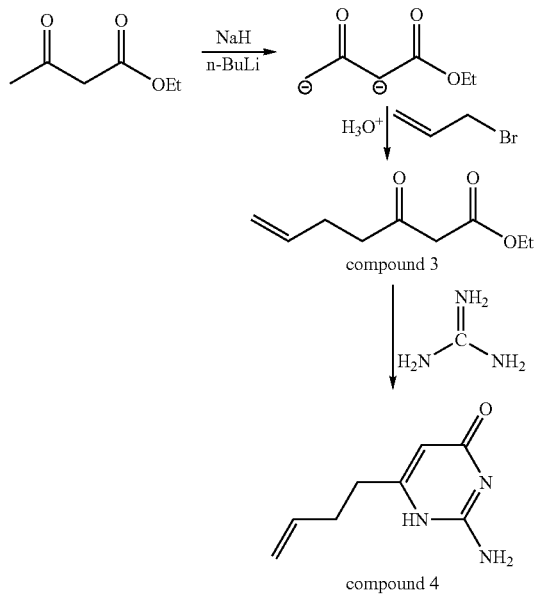

Synthesis of α-ω-di(4-benzyloxy-6-butyl-2-butylurefdopyrimidinyl)poly(dimethylsiloxane) (Compound 2-Bn)

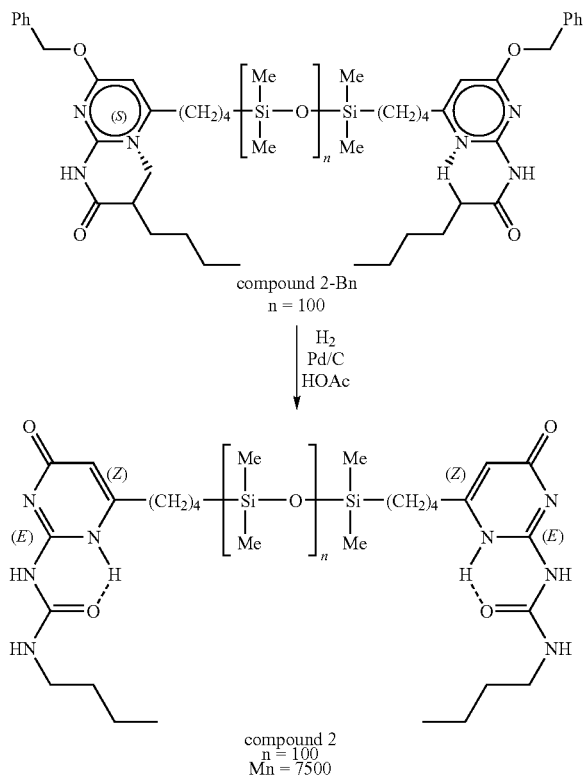

Syntheses of α,ω-di(6-butyl-2-butylureïdo-4-pyrimidinoyl)poly(dimethylsiloxane) (Compound 2)

Operating Mode

Preparation of Compound 3

Compound 3 is prepared following the method described in the article by HUCHIN, S. N., J. Am. Chem. Soc., 96 1082, 1974 (bp 106-108° C., 15 mmHg, lit. 106-108° C.); $^1$H NMR (CDCl$_3$): δ 5.82 (m, 1H, HC=CH$_2$), 5.01 (m, 2H, CH2=CH), 4.20 (q, 2H, OCH$_2$), 3.45 (s, 2H, CH$_2$), 2.66 (t, 2H, CH$_2$), 2.34 (m, 2H, CH$_2$), 1.30 (t, 3H, CH$_3$) ppm; $^{13}$C NMR (CDCl$_3$): δ 202.4, 167.6, 137.1, 116.04, 61.9, 49.9, 42.5, 27.92, 14.6 ppm; IR (Kbr); ν=3,040, 2981, 1744, 1641, 1236 cm$^{-1}$.

Preparation of Compound 4

In a three necked reactor, 18.02 g of guanidine carbonate are introduced (i.e., 0.10 mol). Scanning by a nitrogen stream, followed with a sealing by a septum. 200 ml of dry ethanol are added. Then, under stirring, ethyl-3-oxo-6-heptenoate (resulting from the reaction of 26 g, 0.2 mol of ethyl acetoacetate) is slowly added. The mixture is then vigorously stirred, then heated at reflux for 24 hours. Part of the solvent is distilled and the product is precipitated through addition of water. The precipitate is filtered, washed with water, with cold ethanol and cold acetone and vacuum dried (13.73 g, 42%).

Preparation of Compound 5

2.86 ml of butyl isocyanate are slowly added (i.e. 25.4 mmol) to a solution containing 3.0 g of compound 4 (i.e. 18.2 mmol) in 36 ml of (dried) pyridine. The mixture is heated at reflux for 3 hours. The pyridine is removed through evaporation. The raw product is recrystallized from ethanol to give 4.2 g (87%) of compound 5.

Preparation of Compound 6

Using a syringe, 1.58 ml of benzyl bromide (i.e. 13.24 mmol) are added to a suspension containing 1.0 g of compound 5 (i.e. 3.8 mmol) and 1.83 g of potassium carbonate (i.e. 13.24 mmol) in 25 ml of (dry) DMF. The suspension is vigorously stirred at a temperature of 80° C. for 24 hours. Then acetone is added in the reaction mixture and the thus obtained suspension is filtered. The residue is washed with DMF and acetone. Then, water is added to the filtrate. The white precipitate is filtered and washed with water. A the filtrate. The white precipitate is filtered and washed with water. A recrystallisation from the methanol/water mixture (3:1 v/v), followed by the recrystallisation from hexane gives 1.04 g of pure compound 6 (i.e. a 78% reaction yield).

Preparation of Compound 2-Bn

In a glove box, a solution is produced by mixing:
- 27 g of poly(dimethylsiloxane)dihydride, i.e. 4.5 mmol (originating from ABCR, number average molecular mass is 6000),
- 23.92 g, i.e. 67.49 mmol, of compound 6,
- 136 μl of a solution of platinum catalyst PCO72 (originating from ABCR) to 2.1-2.4% in xylene, and
- 135 ml toluene.

Upon the exit from the glove box, the vessel containing said solution is heated at 80° C. for 24 hours under a nitrogen atmosphere.

The resulting product is evaporated from its solvent, and then washed three times with 30 ml methanol. 24.42 g of compound 2-Bn are then obtained in the form of a low viscosity oil which does not show any impurity at the NMR analysis (i.e. a 90% yield).

Preparation of Compound 2

10 g of compound 2-Bn (i.e. 1.17 mmol), 0.11 g of Pd/C (10% in weight, 0.1 mmol), 100 ml of THF, 50 ml of ethanol and 0.03 g of acetic acid (i.e. 0.5 mmol) are mixed together and then loaded in a Parr reactor. The reaction mixture is washed several times with nitrogen and then with hydrogen. The reactor has been stirred for 24 hours under a hydrogen atmosphere at a pressure of approximately 4 atm. After filtration of the catalyst, the solvent is evaporated. The raw reaction product is then dissolved in a dichloromethane/ethanol mixture (3:1), and the dichloromethane is then evaporated. The final compound precipitates at the bottom of the flask and the top layer, comprising ethanol, is removed. After vacuum drying, 9 g of a very viscous oil are obtained. Purity checking through NMR.

Example 3

Preparation of a Polyester Having Two α,ω-OH Ends with Ureidopyrimidone Groups

A) Synthesis of the Polyester with Initial α,ω-OH Ends: Sebacate/Terephthalate Copolymer of Neopentylglycol (MW=600-700) and with α,ω-OH Ends Reactive Agents

| | |
|---|---|
| Dimethyl terephthalate | 116.4 g (0.6M) |
| Dimethyl sebacate | 138 g (0.6M) |

-continued

| | |
|---|---|
| 2,2-dimethyl-1,3-propanediol (or neopentylglycol) | 274.6 g (2.64M) |
| Zinc acetate dihydrate (0.3% in weight/reactive agent) | 1.6 g |
| pure 1, dichloroethane | 2 l |
| Permuted water | 2 l |

Operating Mode

A 500 ml cylindrical reactor is used, which is provided with a nitrogen inlet, a thermometer and a distillation assembly. The reactor is heated in a Wood alloy bath.

In the reactor are introduced the 2,2-dimethyl-1,3-propanediol (melting point 126-128° C.) and the previously molten methylsebacate (melting point 25-28° C.). The mixture is heated from room temperature to 150° C. in one hour. As soon as the reaction medium becomes clear at approximately 100° C., the dimethyl terephthalate is added. As soon as a 150° C. temperature is reached in the reaction, then the zinc acetate is added. The synthesis is allowed to proceed for three hours at 150° C. while collecting the formed methanol. Then, the temperature is increased to 200° C. in forty-five minutes and is then held for three hours at 200° C. The distillation of the methanol goes on proceeding during the whole condensation.

At the end of the three hours at 200° C., it is allowed to return to room temperature under reduced stirring. As soon as the inner temperature reaches 50° C., 300 ml of 1,2-dichloroethane are added.

The synthesis solution is recovered and then diluted with 1.7 l of 1,2-dichloroethane. The excess 2,2-dimethyl-1,3-propanediol is then extracted twice with one litre of permuted water. During those extractions, it may happen that an interfacial emulsion is formed. Such an emulsion is easily removable through heating of the water used during the extraction. The organic phase is recovered and dried on anhydrous sodium sulfate. The 1,2-dichloroethane is filtered and evaporated until recovery of the dry product.

The polymer has the form of a paste at room temperature and becomes liquid at 50° C.

Characterisation

| | |
|---|---|
| Hydroxyl index: | 189-192 |
| Molecular weight measured at the peak top through chromatography by steric exclusion: | 600 |

B) Transformation of the α,ω-OH- ends into α, ω Ureidopyrimidone Ends

The procedure is exactly the same as for example No. 1 through successive reactions with the isophorone diisocyanate, then introduction of methylisocytosine, while adapting the amounts to the —OH end rate contained in the oligomer.

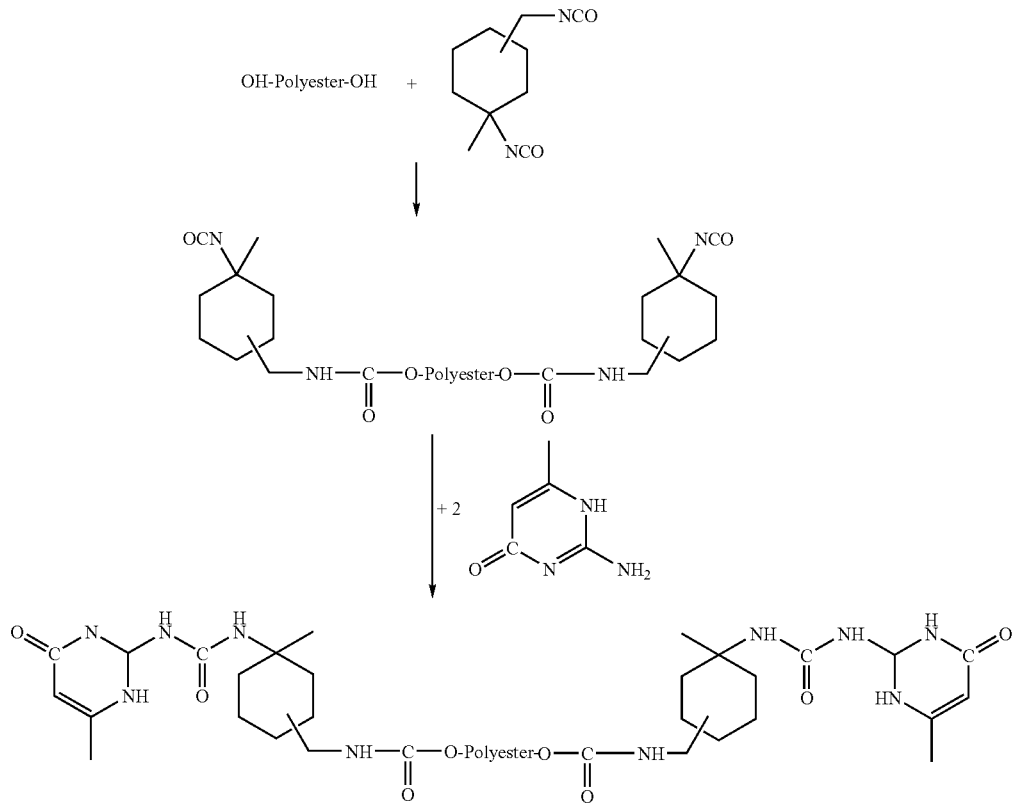

Examples of Cosmetic Composition

Example A

Lipstick

A lipstick is prepared having the following composition:

| | |
|---|---|
| PERFORMALENE 500 ®[(1)] polyethylene wax | 15 g |
| PDMS with ureidopyrimidone ends of example 2 | 5 g |
| Pigments | 9 g |
| Hydrogenated polyisobutylene oil[(2)] | 35.5 g |
| Phenyltrimethicone Dow 556 Fluid ®[(3)] oil | 35.5 g |

[(1)]sold by the PETROLITE corporation
[(2)]with a 34 mm²/s (34 cSt) viscosity at 25° C., sold under the trade name << Parleam ® >> by the NIPPON OIL-FATS corporation.
[(3)]sold by the DOW CORNING corporation All the components of the above-described composition are mixed at 110° C. in a pan. After the pigments have been homogenised and crushed, the mixture is cast in an appropriate mould. A stick is thus obtained having good rheological characteristics. It makes it possible to apply on the lips a film which has a good retention over time (the colour does not change and the film does not disappear in contact with saliva and lip friction).

Example B

Lip gloss

A lip gloss is prepared which has the following composition:

| | |
|---|---|
| PDMS with ureidopyrimidone ends of example 2 | 5 g |
| Pigments (DC Red N° 7 Calcium (lacquer)) | 5 g |
| Phenyltrimethicone Dow 556 Fluid ®[(*)] oil | 90 g |

[(*)]commercialised by the DOW CORNING corporation.

The PDMS in example 2 is first dissolved in the oil contained in a vessel. A lip gloss is obtained by dispersing the pigments in such an oily phase. The thus obtained lip gloss can be applied with a brush onto the lips. It provides the lips with a lasting glossy colouration over time.

Example C

Hairstyling gel

A hairstyling gel is prepared which has the following composition:

| | |
|---|---|
| Ureidopyrimidone POE/PPO copolymer in example 1 | 0.2 g |
| Synthalen K[(*)] cross-linked polyacrylate neutralized with aminomethylpropanol | 1 g |
| Ethanol | 17 g |
| Water | qsp 100 g |

[(*)]commercialised by the 3V corporation

The invention claimed is:

1. A cosmetic composition comprising, in a physiologically acceptable medium, at least one linear, or branched, comprising:

a -POL- polymeric backbone comprising at least two repeating patterns, and at least two binding groups (A), attached on the polymeric backbone and capable of forming H links with one or more binding groups, wherein the binding groups (A) may be identical or different and wherein each coupling of two binding groups (A) involves at least three H links, wherein the polymeric backbone is selected from the group consisting of a polydiene, a hydrogenated polydiene, a polyester, a polycarbonate, a polyacetal, a polyoxyalkylene, a polythioether, a perfluoropolyether, a polyolefin, a polyorganosiloxane, a vinyl polymer, a poly(meth)acrylic polymer, and wherein binding groups (A) are selected from the group consisting of adenine, guanine, cytidine, thymine, pterine, ureidopyrimidone, melamine, cyanuric acid, maleimide, phthalhydrazine, isoguanine, glycoluril, uracil, acylaminopyridine, monoacylaminopyridine, bis(acylamino)pyridine, acylaminotriazine, monoacyl-2,4-diamino-s-triazine, bis-acyl-2,4-diamino-s-triazine, urazole, glutarimide, urazoylbenzoic acid, succinimide, 2,4-diamino-s-triazine, ureidotriazine and phthalhydrazine.

2. The cosmetic composition according to claim 1, wherein the -POL- polymeric backbone has a polymerisation degree ranging from 2 to 70,000.

3. The cosmetic composition according to claim 1, wherein the polymer is a bifunctional POE/PPO copolymer having three ureidopyrimidone ends.

4. The cosmetic composition according to claim 1, wherein the polymer is a polydimethylsiloxane having two ureidopyrimidone ends.

5. The cosmetic composition according to claim 1, wherein the polymer is a polyester having two α,ω-ureidopyrimidone ends.

6. The cosmetic composition according to claim 1, wherein the composition is in the form of at least one of an aqueous, alcoholic or hydroalcoholic solution or suspension; an oily solution or suspension; a lotion or a serum; an emulsion having a liquid or semi-liquid milk consistency, obtained through dispersion of a fatty phase in an aqueous phase (O/W) or of an aqueous phase in a fatty phase (W/O); an oil-in-water (O/W) or a water-in-oil (W/O) cream with a soft consistency; an aqueous or anhydrous gel; an ointment; or a free or compacted powder with or without an excipient.

7. The ccosmetic osmetic composition according to claim 1, comprising at least one solvent selected from the group consisting of water, polyols, short esters, hydrocarbon oils, silicone oils, fluorinated silicone oils and the mixtures thereof.

8. The cosmetic composition according to claim 1, comprising at least one builder selected from the group consisting of hydrophilic or lipophilic gellants; hydrophilic or lipophilic active ingredients; preservatives; antioxidants; solvents; perfumes; fillers; odour absorbers; neutralizing agents; and emulsifiers.

9. The cosmetic composition according to claim 8, comprising one or more active ingredients selected from the group consisting of depigmenting agents, emollients, moisturizing agents, antiseborrheic agents, anti-acne agents, hair growth promoting agents, keratolytic agents, desquamative agents, antiwrinkle agents, tensor agents, anti-irritating agents, soothing agents, vitamins, screens, odour absorbers and mixtures thereof.

10. The cosmetic composition according to claim 1, further comprising at least one colouring material selected from the group consisting of lipophilic dyes, hydrophilic dyes, pigments, pearlescent materials and mixtures thereof.

11. The cosmetic composition according to claim 1, in the form of a foundation cream, a blusher, a cheek make-up, an eyelid make-up, an eye-shadow concealer, an eyeliner, a temporary tattoo product for the body skin, a lip make-up product, a dermoskeleton make-up product, or a hair dye product.

12. A composition suitable for applying onto keratin materials comprising the cosmetic composition of claim 1 and one or more dermatologically or physiologically acceptable diluents or additives.

13. The cosmetic composition as claimed in claim 1, wherein the -POL- polymeric backbone has a polymerization degree of from 10 to 5,000.

* * * * *